US010596328B2

(12) United States Patent
Plambech et al.

(10) Patent No.: US 10,596,328 B2
(45) Date of Patent: Mar. 24, 2020

(54) SPRING-DRIVEN DRUG DELIVERY DEVICE (71) Applicant: Novo Nordisk A/S, Bagsvaerd (DK)

(72) Inventors: Christian Plambech, Soeborg (DK); Jesper Peter Windum, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 397 days.

(21) Appl. No.: 15/532,579

(22) PCT Filed: Dec. 22, 2015

(86) PCT No.: PCT/EP2015/080904
§ 371 (c)(1),
(2) Date: Jun. 2, 2017

(87) PCT Pub. No.: WO2016/102526
PCT Pub. Date: Jun. 30, 2016

(65) Prior Publication Data
US 2017/0333639 A1 Nov. 23, 2017

(30) Foreign Application Priority Data

Dec. 22, 2014 (EP) ..................................... 14199612
Feb. 3, 2015 (EP) ..................................... 15153602

(51) Int. Cl.
*A61M 5/315* (2006.01)
*A61M 5/20* (2006.01)
(Continued)

(52) U.S. Cl.
CPC .......... *A61M 5/31583* (2013.01); *A61M 5/20* (2013.01); *A61M 5/2033* (2013.01);
(Continued)

(58) Field of Classification Search
CPC ........ A61M 5/20; A61M 5/2033; A61M 5/24; A61M 5/31528; A61M 5/3155;
(Continued)

(56) References Cited

U.S. PATENT DOCUMENTS 5,104,380 A  4/1992  Holman et al.
6,899,699 B2  5/2005  Enggaard
(Continued)

FOREIGN PATENT DOCUMENTS

CN  102596291 B  11/2014
EP  2600924 A1  6/2013
(Continued)

OTHER PUBLICATIONS

Zhang et al. "Research on dose and depth adjustable needle-free injector." China Mechanical Engineering, 2011, vol. 2, pp. 447-457.

*Primary Examiner* — Shefali D Patel
(74) *Attorney, Agent, or Firm* — Wesley Nicolas (57) ABSTRACT

The present invention relates to a drug delivery device (100) comprising a housing (101), a threaded piston rod (102), a rotatable drive tube (103), a drive nut (104) in threaded engagement with the piston rod (102) and being rotationally locked but axially moveable relative to the drive tube (103), and a support member (105) arranged rotationally free on the piston rod (102), the support member (105) being axially locked relative to the housing (101) and arranged to allow the drive tube (103) to move axially. The device further comprises a compression drive spring (106) arranged between the piston rod (102) and the drive tube (103), the compression drive spring (106) being arranged axially between the drive nut (104) and the support member (105).

10 Claims, 3 Drawing Sheets

(51) Int. Cl.
 *A61M 5/24* (2006.01)
 *A61M 5/31* (2006.01)
(52) U.S. Cl.
 CPC .......... *A61M 5/24* (2013.01); *A61M 5/31551* (2013.01); *A61M 5/31553* (2013.01); *A61M 2005/2407* (2013.01); *A61M 2005/2411* (2013.01); *A61M 2005/3125* (2013.01)
(58) Field of Classification Search
 CPC .......... A61M 5/31551; A61M 5/31553; A61M 5/31578; A61M 5/3158; A61M 5/31583; A61M 5/31585
 See application file for complete search history.

(56) References Cited

U.S. PATENT DOCUMENTS

| | | |
|---|---|---|
| 8,608,708 B2 | 12/2013 | Cowe |
| 2010/0114038 A1 | 5/2010 | Sams |
| 2013/0211342 A1 | 8/2013 | Raab et al. |

FOREIGN PATENT DOCUMENTS

| | | |
|---|---|---|
| JP | H0271758 A | 3/1990 |
| JP | 2004516895 | 6/2004 |
| WO | 2008037801 A1 | 4/2008 |
| WO | 2011/060786 A1 | 5/2011 |
| WO | 2012017036 A1 | 2/2012 |
| WO | 2012089616 A1 | 7/2012 |
| WO | 2014166914 A1 | 10/2014 |
| WO | 2014191189 A1 | 12/2014 |
| WO | 2015075134 A1 | 5/2015 |

SPRING-DRIVEN DRUG DELIVERY DEVICE

CROSS-REFERENCE TO RELATED APPLICATIONS

This application is a 35 U.S.C. § 371 National Stage application of International Application PCT/EP2015/080904 (published as WO 2016/102526), filed Dec. 22, 2015, which claims priority to European Patent Application 14199612.4, filed Dec. 22, 2014, and European Patent Application 15153602.6, filed Feb. 3, 2015; the contents of which are incorporated herein by reference.

The invention relates to a drug delivery device for delivering set doses of a liquid drug. The drug delivery device is preferably of the type in which a drive tube during drug ejection is rotated using a drive spring moving a piston rod forward.

BACKGROUND OF THE INVENTION

In the disclosure of the present invention reference is mostly made to the treatment of diabetes by delivery of insulin or other diabetes drugs, however, this is only an exemplary use of the present invention.

Drug delivery devices in the form of injection devices for subcutaneous administration of fluid drugs have greatly improved the lives of patients who must self-administer drugs and biological agents. Drug injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices are generally of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded.

A further distinction can be made for the drive means delivering the force to move the cartridge piston forwards during expelling of a dose of drug. Traditionally injection devices have been manually actuated by the user pushing an extendable button during expelling, however, alternatively the driving force may be provided by a spring being pre-strained or strained during dose setting and subsequently released, this allowing for "automatic" dispensing of drug.

Despite their advantages such automatic drug delivery devices "compete" on size with the more traditional devices for multiple uses without any auto dosing feature. Therefore there is a desire to provide smaller automatic drug delivery devices which may be realized by new designs of the expelling mechanisms.

Correspondingly, drug delivery devices have been proposed that aims at reducing the size by utilising a compression drive spring or the like to deliver the drug automatically. However, the compression drive spring force and an activation force responsible for activating delivery of the drug often both will be axially working forces acting on a common element from opposite directions, e.g. for pen or pen-like drug delivery devices having an end-mounted release button. In such devices, a compression drive spring will even provide an axial force that increases linearly with the set dose. Therefore, a user wishing to activate the drug delivery must work against and even overcome this relatively high force, and even higher with higher doses, in order to activate the drug delivery.

As an example, WO 2011/060786 discloses an "autopen" driven by a compression spring strained during dose setting, the pen comprising a drive nut in threaded engagement with a piston rod, the drive nut being rotationally locked but axially moveable relative to a drive tube. The compression drive spring is arranged inside the drive tube and acting between the drive nut and the proximal end of the drive tube. When a set dose is released the drive tube is moved distally against the force of the spring and into engagement with the drive member to thereby rotate the piston rod.

Having regard to the above, it is an object of the present invention to provide an automatic drug delivery device that reduces the axial force needed to release an expelling mechanism comprising a compression drive spring. The device should be reliable in use and should be provided in a cost-effective manner. Certain designs for such drug delivery devices involve the use of a rotating drive tube for automatic drug delivery which complicates matters further. Correspondingly, it is a further object of the present invention to reduce the force needed to release an expelling mechanism of the above type using a rotating drive tube.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a drug delivery device is provided comprising a housing, a threaded piston rod defining an axial direction and having a proximal end and a distal end, a rotatable drive tube, and a drive nut in threaded engagement with the piston rod and being rotationally locked but axially moveable relative to the drive tube. The device further comprises a support member arranged rotationally free on the piston rod and arranged to allow the drive tube to move axially, the support member being arranged axially stationary relative to the housing and arranged to allow the drive tube to move axially, a compression drive spring arranged between the piston rod and the drive tube, the compression drive spring being arranged axially between the drive nut and the support member, and dose setting means allowing a user to set a dose amount of drug to be expelled, the compression drive spring being strained corresponding to the dose being set.

By this arrangement a drug delivery device is provided in which no force is transferred between the support member and the drive tube but where the force from the compression drive spring is diverted to the housing via the support member, thereby enabling that a user does not need to work against and overcome a force from the compression drive spring when activating the device.

Additionally, this is provided while maintaining a rotating drive tube as a functional element even though it comprises the compression drive spring.

Furthermore, this is enabled while having a compression drive spring arranged inside the rotating drive tube and having an available housing only outside the drive tube.

In some embodiments, the rotation of the drive tube in a dose setting direction results in the drive nut being moved proximally on the piston rod thereby straining the compression drive spring between the drive nut and the support member.

In some embodiments, the drug delivery device further comprises a drive member being rotationally locked but axially moveable relative to the piston rod, and wherein the drive tube can be moved distally from a dose setting position to a drive position in which the drive tube can axially engage the drive member and where the drive tube and the drive member are rotationally locked in relation to each other but where both are allowed to rotate together.

In some embodiments, the following takes place when the drive tube is moved distally from the dose setting position to the drive position: (i) the piston rod, the drive tube, the drive nut, and the drive member are rotationally locked, and (ii) a distally directed force from the compression drive spring results in the piston rod, the drive tube, the drive nut, and the drive member being rotated whereby a threaded interface in the housing will move the piston rod distally.

In some embodiments, the drive tube comprises an opening allowing a portion of the support member to engage a housing portion outside the drive tube.

In some embodiments, the support member is allowed to rotate relative to the housing.

In some embodiments, the drug delivery device further comprises a drug delivery activation element adapted to rotate the drive tube in the dose setting direction via a coupling element rotationally engaging the drive tube in the dose setting position, and where the drive tube is distally and axially moved upon dose activation in the drive position, whereby the coupling element no longer will engage the drive tube.

In some embodiments, the coupling element is a ratchet element which may form part of a two-way ratchet allowing a set dose to be adjusted.

In some embodiments, the coupling element prevents the drive tube from rotating until dose activation after which the drive tube will be in the drive position and will rotate also rotating the drive member.

In some embodiments, the support member comprises a protrusion that engages or mates the housing or the housing portion.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs. Correspondingly, the term "subcutaneous" infusion is meant to encompass any method of transcutaneous delivery to a subject.

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries. "Injection pens" are examples of "drug delivery devices".

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Using the term "automatic" in conjunction with injection device means that the injection device is able to perform the injection automatically without the user of the injection device delivering the force needed to expel the drug. The force may be delivered by a spring as herein described. The spring is usually strained by the user during dose setting, however, such springs are usually pre-strained in order to avoid problems of delivering very small doses. Alternatively, the spring can be fully preloaded by the manufacturer with a preload sufficient to empty the drug cartridge through a number of doses. Typically, the user activates a latch mechanism e.g. in the shape of a button on the injection device to release the force accumulated in the spring when carrying out the injection. The release mechanism can also be coupled to a proximally located injection button.

All references, including publications, patent applications, and patents, cited herein are incorporated by reference in their entirety and to the same extent as if each reference were individually and specifically indicated to be incorporated by reference and were set forth in its entirety herein.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

In the following embodiments of the invention will be described with reference to the drawings, wherein.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. In that context it may be convenient to define that the term "distal end" in the appended figures is meant to refer to the end of the injection device which usually carries the injection needle and as depicted e.g. in FIG. 1B whereas the term "proximal end" is meant to refer to the opposite end pointing away from the injection needle. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part.

Before turning to embodiments of the present invention per se, an example of a "generic" drug delivery device will be described, such a device providing the basis for the exemplary embodiment of the present invention.

Figure 1A:
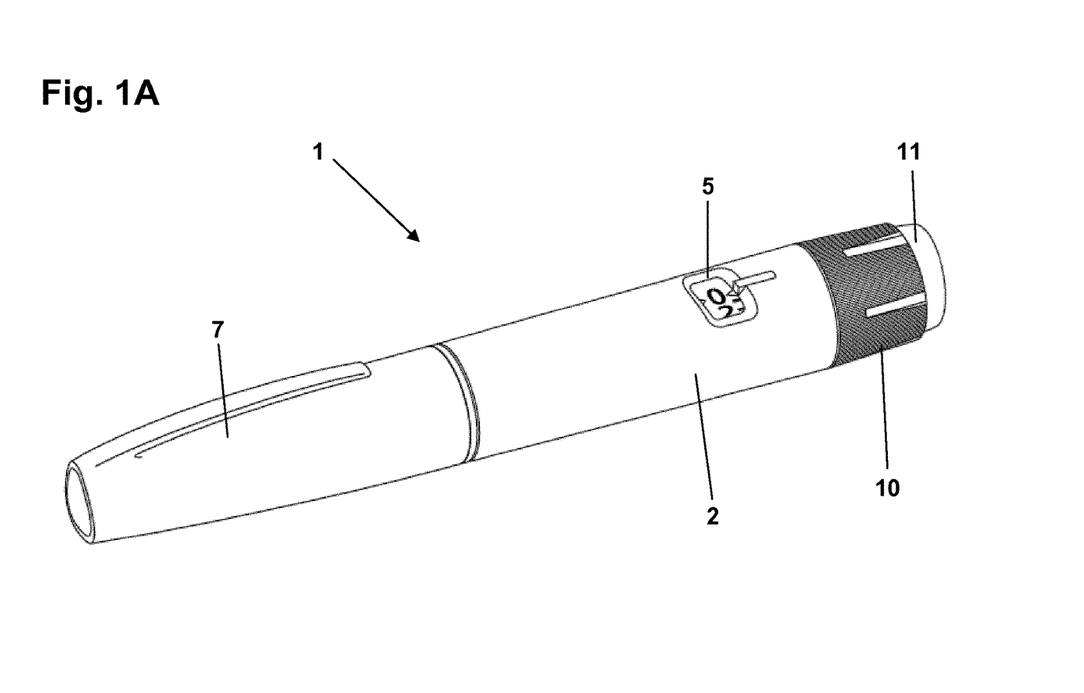
FIGS. 1A and 1B show an embodiment of a generic drug delivery device.
Figure 1B:
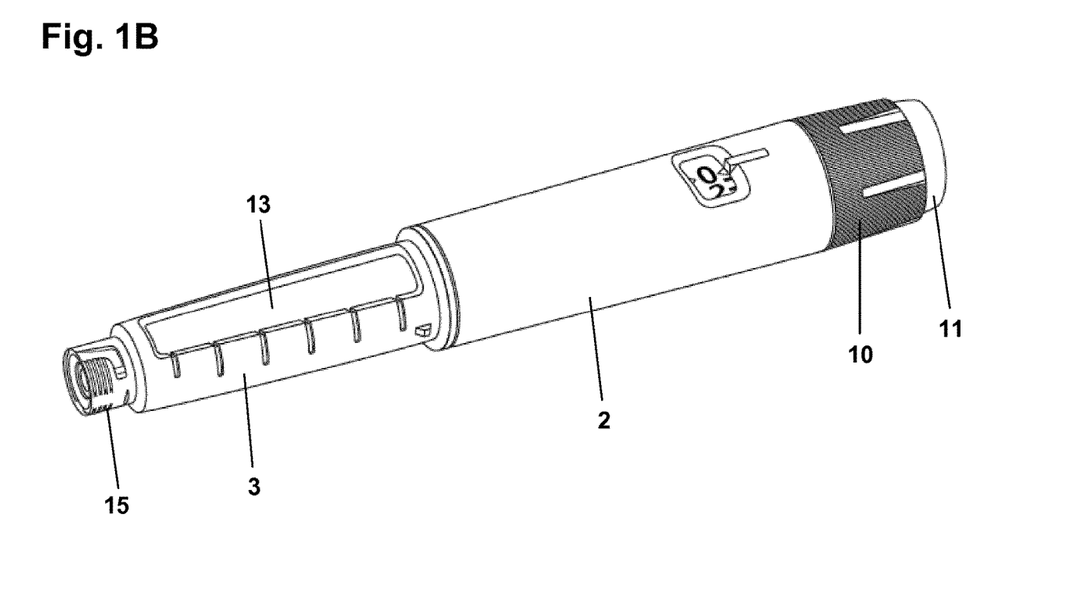

The pen device 1 comprises a cap part 7 and a main part having a proximal body or drive assembly portion with a housing 2 in which a drug expelling mechanism is arranged or integrated, and a distal cartridge holder portion in which a drug-filled transparent cartridge 13 with a distal needle-penetrable septum is arranged and retained in place by a cartridge holder attached to the proximal portion, the cartridge holder having openings allowing a portion of the cartridge to be inspected. Distal coupling means 15 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 10 serves to manually set a desired dose of drug shown in display window 5 and which can then be expelled when the button 11 is actuated. Alternatively the dose setting member and actuation member may be in the form of a combined dose setting and actuation member. The shown device comprises an expelling mechanism provided with a drive spring which is strained during dose setting and then released to drive the piston rod when the release button is actuated.

Although FIGS. 1A and 1B show a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

Figure 2:
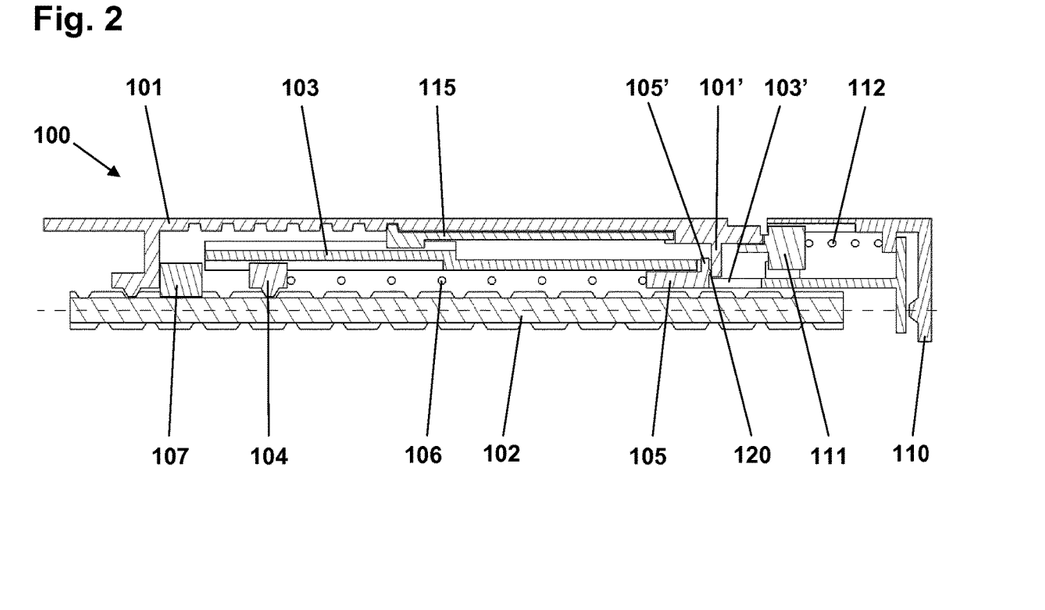
FIG. 2 shows a cross-section schematically illustrating in part an embodiment of a spring-driven drug delivery device in a rest state.

FIG. 2 shows a cross-section schematically illustrating a part of one embodiment of drug delivery device in a rest state. More specifically, FIG. 2 shows a part of a drug delivery device 100 comprising a housing or frame 101 (throughout the text simply referred to as housing) encompassing the various components of the drug delivery device 100. The housing 101 may be a part of or be comprised by an outer or overall housing of the drug delivery device 100. In FIGS. 1-4 the distal is oriented to the left while the proximal end is oriented to the right.

As shown, the drug delivery device 100 further comprises a threaded piston rod 102, a rotatable drive tube 103, a drive nut 104, a support member 105, and a compression drive spring 106. The piston rod during dosing activates a plunger in a cartridge containing the liquid drug to be delivered or some other suitable drug delivery mechanism.

The drive nut 104 is in threaded engagement with the piston rod 102 by an outer thread on the piston rod and an internal thread on the drive nut such that the drive nut is moved axially when rotated relatively to the piston rod during dose setting. The drive nut is rotationally locked but axially moveable relative to the drive tube 103 via a splined connection.

The support member 105 is arranged rotationally free on the piston rod 102 while being arranged axially stationary relative to the housing 101. Furthermore, the support member 105 is arranged to allow the rotatable drive tube 103 to move axially relative to the support member and the housing. The generally tubular compression drive spring 106 is arranged circumferentially between the piston rod 102 and the drive tube 103 and axially between the drive nut 104 and the support member 105.

In certain embodiments and as shown in FIG. 2, the support member 105 is allowed to rotate relative to the housing 101 while the drive tube 103 and the support member are tangentially locked (there may e.g. be some slip or play as long as they will engage each other rotationally at some point) in relation to each other. Hereby, the support member and the drive tube are rotatable together but can only move axially in relation to each other with the drive tube moving axially in relation to the support member and the housing.

In the shown embodiment the support member 105 has a number of lateral projections 105' arranged through corresponding longitudinal openings 103' in the drive tube, each projection having a proximally-facing surface engaging the distally-facing surface of a circumferential inner flange portion 101', the two structures being held in engagement by the compression spring 106. In the shown embodiment the support member projections 105' comprises a small protrusion 120 or similar that rotationally engages or mates (as one or more bearing surfaces) with the housing inner flange 101'. A bearing or the like may also be inserted between the support member 105 and the housing/housing portion 101, 101' instead of the protrusions in order to reduce friction.

In the shown embodiment the drive tube 103 is generally shaped as a distal cylinder portion adjoining a smaller intermediate cylinder portion adjoining yet an even smaller proximal cylinder portion with grooves or tracks, e.g. splines, formed in the distal portion for engaging at least the drive nut 104, the drive member 107 and the indicator element 115 as will be described.

It is of course to be understood that the shape(s) of the drive tube 103, the support member 105, and other elements of the drug delivery device housing 101 may be varied in different embodiments, configurations and implementations.

The embodiment of a drug delivery device shown in FIG. 2 further comprises a dose or drug delivery activation element 110, e.g. a proximally located button or similar, that a user activates, in these particular exemplary embodiments, by pressing it axially in the distal direction. A bias spring or other resilient member 112 is present to push the activation element 110 back to its resting position as shown in FIG. 2. Drug delivery activation and actual delivery is shown and explained further in connection with FIG. 4, where the drug delivery device 101 is shown in a position also referred to as a drive position throughout the description and claims. As will be explained further later and in connection with FIG. 4, the activation and delivery involves use of the rotating drive tube 103. A dose setting indicator element 115 indicates to a user what dose to be delivered is currently selected. When the dose setting element 110 is used to set the dose, the indicator element 115 will be moved accordingly via rotation of the drive tube 103, see FIGS. 2 and 3, the indicator element being in splined connection with the drive tube and helically coupled to an interior surface of the housing.

As shown and described, the compression drive spring 106 engages the support member 105 axially in the proximal direction and thereby transfer its action force (due to being compressed) to the support member 105 while the activation force of the user is axially directed in the distal direction. However, since the support member 105 is axially locked relative to the housing 101, i.e. it engages the housing 101 axially, the action force of the compression drive spring 106 will be transferred to the housing 101 via the support member 105 in an arrangement of the drug delivery device where the housing 101 only is available outside but where the compression drive spring 106 is being arranged inside drive tube 103, respectively.

Since the support member 105 is not constrained to the rotating drive tube 103 axially, but rather they are free to move axially in relation to each other, then no (compression drive spring) force can be transferred from the support member 105 to the rotating drive tube 103. In embodiments where it is required that the drive tube 103 during drug delivery will rotate more than one complete revolution, the drive tube 103 and the support member 105 should still be constrained rotationally, as shown in FIG. 2, in order for the drug delivery mechanism to function properly. Preferably, the drive tube 103 comprises an opening 103' readily allowing a portion 105' of the support member 105 to engage a housing portion 101' outside the drive tube 103.

Furthermore, since the (axially opposite) activation force involves use of the rotating drive tube 103 there will not be any oppositely directed forces from the compression drive spring 106 and the user activation and therefore the user will not need to work against and overcome the force from the compression drive spring when activating the device as the force from the compression drive spring is diverted to the housing 101 via the support member 105.

Additionally, this is even provided while maintaining a rotating drive tube 103 as a functional element also in relation to the activation and drug delivery, which has its advantages. Furthermore, this is enabled while having a compression drive spring 106 arranged inside the rotating drive tube 103 and having an available housing 101 only outside the drive tube. These components (addressing the issue of having to overcome the spring force during activation) may generally be used with different piston drive systems, different compression systems etc.

The compression drive spring 106 may be compressed using many different systems depending on specific implementations. This stores energy in the compression drive spring 106 that, when released again, will activate drug delivery.

As shown in the embodiment of FIG. 2, rotation of the drive tube 103 (by a user) in a dose setting direction will move the drive nut 104 proximally on the piston rod 102 due to the driving tube 103 engaging the drive nut 104 rotationally (and also since the drive nut 104 is able to move axially relative to the driving tube 103 and is in a threaded engagement with the piston rod 102). This proximal movement of the drive nut 104 on the piston rod 102 will strain the compression drive spring building up energy to be used in automatically delivering the drug of the device. The drug delivery device 101 during dose setting is illustrated and explained further in connection with FIG. 3.

In certain embodiments and as shown in FIG. 2, the drug delivery device 100 further comprises a drive member 107 being rotationally locked but axially moveable relative to the piston rod 102 and wherein the drive tube 103 can be moved distally from a dose setting position (see FIG. 3) to a drive position (see FIG. 4) in which it can non-rotationally engage the drive member 107.

When the drive member 103 is moved distally from the dose setting position to the drive position the following takes place: The drive tube 103 is moved into rotationally locked engagement with the drive member 107 whereby the drive tube 103 is allowed to rotate the drive member 107. The piston rod 102, the drive tube 103, the drive nut 104, and the drive member 107 are all rotationally locked in this situation. A distally directed force from the compression drive spring 106, i.e. the force from the energy stored in it during dose setting, acting on the drive nut results in the drive nut 104 and thereby also the piston rod 102, the drive tube 103 and the drive member 107 being rotated, whereby a threaded interface 125 in the housing will move the piston rod 102 distally, which will cause a liquid drug to be delivered using a suitable delivery system, which may be different and depending on specific implementation.

In some embodiments, and as shown in FIG. 2, the drug delivery device further comprises a dose setting element 110 rotatably mounted to the proximal end of the housing 101 and by which element the user can set a specific dose to be injected. The dose setting element may alternatively be located elsewhere. In the particular embodiment of FIG. 2 the dose setting element and the dose activation element are the same. Alternatively, two separate elements may be used.

In certain embodiments, again as shown in FIG. 2, the dose setting element 110 may be coupled to the drive tube 103 via a suitable coupling element 111, e.g. like a ratchet element as shown in FIG. 2. The ratchet element may form part of a two-way ratchet mechanism whereby rotation of the dose setting element in a predetermined dose setting direction will set the dose by rotating the drive tube and strain the spring correspondingly by moving the drive nut proximally to thereby compress the drive spring, the ratchet element providing that the drive tube and the strained spring can be "parked" corresponding to the set dose. Correspondingly, rotation of the dose setting element in the opposite direction will reduce a set dose.

Figure 3:
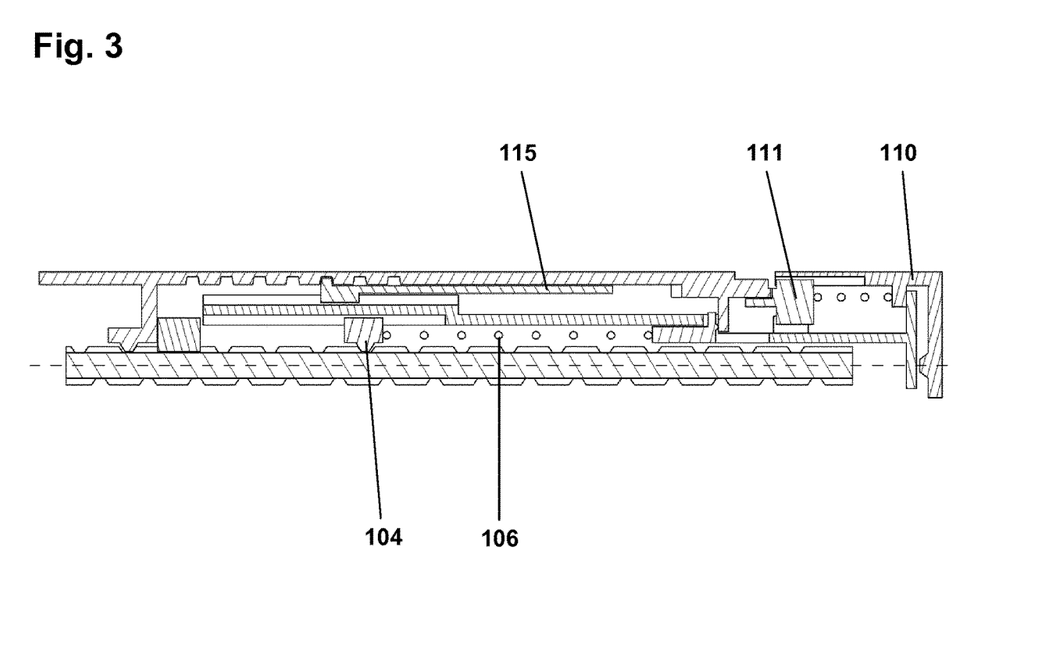
FIG. 3 shows a cross-section schematically illustrating the drug delivery device of FIG. 2 in a dose setting state.
Figure 4:
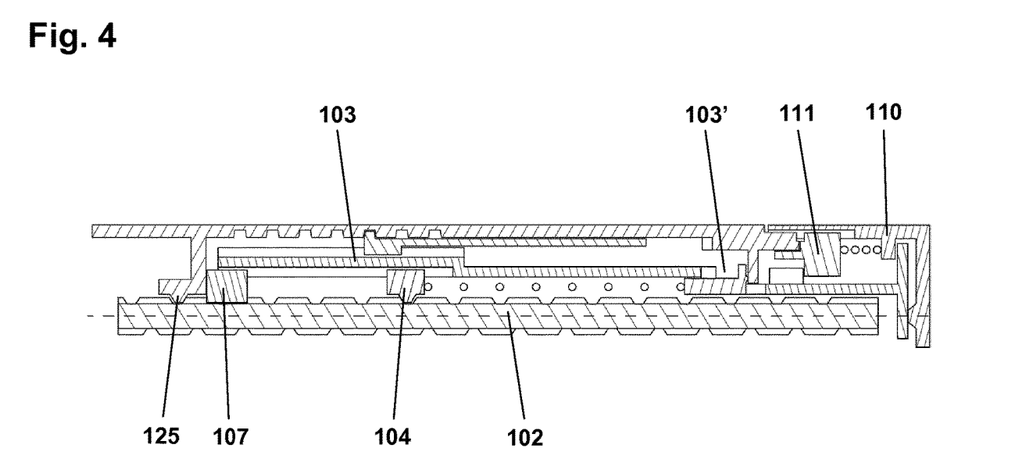
FIG. 4 shows a cross-section schematically illustrating the drug delivery device of FIGS. 2 and 3 in a drive state.
Figure 5:
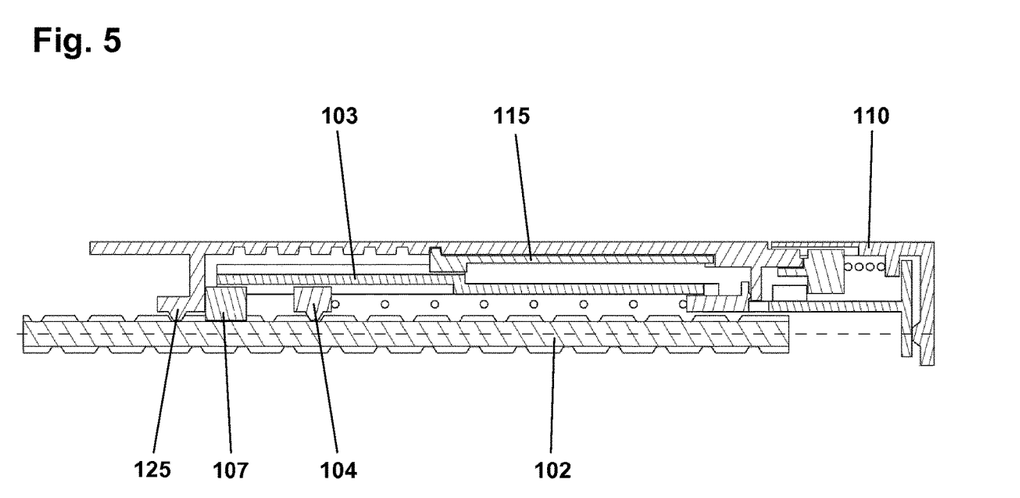
FIG. 5 shows a cross-section schematically illustrating the drug delivery device of FIGS. 2-4 after delivering a dose of liquid drug.

The function of the shown elements of FIG. 2 will be illustrated in FIGS. 3-5 for dose setting, dose activation and delivery, and end of drug delivery, respectively.

FIG. 3 is a cross-section schematically illustrating the drug delivery device of FIG. 2 in a state in which a dose has been set. During dose setting, a user turns the dose setting element 110 (that also functions as the drug delivery activation element) in the dose setting direction, which will rotate the drive tube 103 via the coupling element/ratchet 111. Rotation of the drive tube during dose setting will rotate the drive nut 104 (and the support member 105) whereby the drive nut will move it in the proximal direction on the piston rod 102 which will strain the compression drive spring 106 located between the drive nut and the support member, building up energy to be used subsequently in automatically delivering the drug of the device. Until dose activation is done, the coupling element or ratchet 111 will prevent the drive tube 103 from rotating backwards. In the dose setting state rotation of the drive tube will not rotate the drive member 107 (and thereby the piston rod 102) as they are not engaged. After having turned the dose setting element 110 corresponding to a desired dose of liquid drug to be delivered (e.g. as indicated by the dose setting indicator element 115 also rotated by the drive tube 103) the user is ready to activate drug delivery as will be explained with reference FIG. 4.

FIG. 4 is a cross-section schematically illustrating the drug delivery device of FIGS. 2 and 3 in an initial drive state. To expel a set dose of drug the user will activate the combined dose setting and drug delivery activation element 110 (also being coupling/ratchet element) by pressing it in the distal direction thereby also moving the drive tube 103 in the distal direction. Doing so the following will happen: Firstly the activation element will engage the housing to rotationally lock the activation element and ratchet relative to the housing to thereby prevent any unintended dose adjustment, secondly the drive tube will engage the drive member 107 to rotationally lock the drive member to the drive tube 103, and thirdly the drive tube will disengage from the ratchet to thereby allow the drive tube to rotate relative to the housing, the drive tube being rotated by the drive nut 104 being moved distally by the axially expanding drive spring. As the drive nut, the drive tube, the drive member and the piston rod are rotationally locked relative to each other, also the piston rod will rotate, this resulting in the piston rod being moved distally due to the threaded engagement 125 with the housing. During drug delivery, the dose setting indicator element 115 gradually rotate back via its engagement with the drive tube and the housing.

During activation the support member 105 is not moved distally as it is not axially locked to the drive tube 103, the drive tube thereby being moved distally relative to the support member. Rotationally they will still follow each other. The support member 105 will all the time rest or abut against the housing portion 101' during rotation.

As the compression spring expands the drive nut 104 rotates on the piston rod which again rotates relative to the housing, the drive nut thereby moving distally relative to the drive tube via their splined connection. Expansion of the compression drive spring will continue until the drive nut 104 (and other elements) reach their initial positions (apart from the piston rod) whereby drug delivery will stop as shown in FIG. 5. At the same time the dose setting indicator element 115 reaches a resting position against the housing 101.

In the shown embodiment, the user needs to keep the activation element 110 pressed as long as dosing is carried out to keep the coupling/ratchet element 111 and the drive tube 103 disengaged. However, this may be different in other embodiments.

FIG. 5 shows a cross-section schematically illustrating the drug delivery device of FIGS. 2-4 after delivering a set dose of liquid drug.

After finishing the set drug delivery, the drug delivery device simply needs to be reset to its rest position as shown in FIG. 2. In the shown embodiment this simply involves the user stop pressing the drug delivery activation element 110 as the spring or other resilient member 112 simply will push the activation element back to its resting position as shown in FIG. 2 and with it the drive tube 103.

In the claims enumerating several features, some or all of these features may be embodied by one and the same element, component or item. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, elements, steps or components but does not preclude the presence or addition of one or more other features, elements, steps, components or groups thereof.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device, comprising:
   a housing,
   a threaded piston rod defining an axial direction and having a proximal end and a distal end,
   a rotatable drive tube,
   a drive nut in threaded engagement with the piston rod and being rotationally locked but axially moveable relative to the drive tube,
   a drive member being rotationally locked but axially moveable relative to the piston rod,
   a support member arranged rotationally free on the piston rod and arranged to allow the drive tube to move axially, the support member being arranged axially stationary relative to the housing and arranged to allow the drive tube to move axially,
   a compression drive spring arranged between the piston rod and the drive tube, the compression drive spring being arranged axially between the drive nut and the support member, and
   dose setting structure allowing a user to set a dose amount of drug to be expelled, the compression drive spring being strained corresponding to the dose being set,
   wherein the drive tube can be moved distally from a dose setting position to a drive position in which the drive tube non-rotationally engages the drive member and is allowed to rotate therewith.

2. The drug delivery device as in claim 1, wherein during dose setting rotation of the drive tube in a dose setting direction results in the drive nut being moved proximally on the piston rod thereby straining the compression drive spring between the drive nut and the support member.

3. The drug delivery device as in claim 2, wherein the drug delivery device further comprises a drug delivery activation element adapted to rotate the drive tube in the dose setting direction via a coupling element rotationally engaging the drive tube in the dose setting position, and wherein the drive tube is distally and axially moved upon dose activation in the drive position, whereby the coupling element no longer will engage the drive tube.

4. The drug delivery device as in claim 3, wherein the coupling element is a ratchet element.

5. The drug delivery device as in claim 4, wherein the coupling element prevents the drive tube from rotating until dose activation after which the drive tube will be in the drive position and will rotate also rotating the drive member.

6. The drug delivery device as in claim 1, whereby when the drive tube is moved distally from the dose setting position to the drive position the following takes place:
- the piston rod, the drive tube, the drive nut, and the drive member are rotationally locked, and
- a distally directed force from the compression drive spring results in the piston rod, the drive tube, the drive nut, and the drive member being rotated whereby a threaded interface in the housing will move the piston rod distally.

7. The drug delivery device as in claim 1, wherein the drive tube comprises an opening allowing a portion of the support member to engage a housing portion outside the drive tube.

8. The drug delivery device as in claim 1, wherein the support member is allowed to rotate relative to the housing.

9. The drug delivery device as in claim 1, wherein the support member comprises a plurality of proximally-facing protrusions engaging the housing or a housing portion.

10. The drug delivery device as in claim 1, further comprising a drug reservoir or structure for receiving the drug reservoir, the drug reservoir comprising an outlet portion.

* * * * *